(12) United States Patent
Agathos (10) Patent No.: US 8,585,757 B2
(45) Date of Patent: Nov. 19, 2013

(54) SUPPORT SYSTEM FOR BIOPROSTHETIC VALVES WITH COMMISURAL POSTS WITH HEART-SHAPED OPENINGS (76) Inventor: Efstathios-Andreas Agathos, Filothei Attikis (GR)

( * ) Notice: Subject to any disclaimer, the term of this patent is extended or adjusted under 35 U.S.C. 154(b) by 0 days.

(21) Appl. No.: 13/508,867

(22) PCT Filed: Nov. 9, 2010

(86) PCT No.: PCT/GR2010/000050
§ 371 (c)(1),
(2), (4) Date: May 9, 2012

(87) PCT Pub. No.: WO2011/058385
PCT Pub. Date: May 19, 2011

(65) Prior Publication Data
US 2012/0232646 A1    Sep. 13, 2012

(30) Foreign Application Priority Data
Nov. 11, 2009 (GR) ................ 20090100617

(51) Int. Cl.
*A61F 2/24* (2006.01)
(52) U.S. Cl.
USPC .......................................... 623/2.17
(58) Field of Classification Search
USPC ................................. 623/2.1–2.42
See application file for complete search history.

(56) References Cited

U.S. PATENT DOCUMENTS

| | | | |
|---|---|---|---|
| 6,334,873 B1 * | 1/2002 | Lane et al. | 623/2.14 |
| 2003/0055496 A1 * | 3/2003 | Cai et al. | 623/2.19 |
| 2003/0109922 A1 * | 6/2003 | Peterson et al. | 623/2.17 |

* cited by examiner

*Primary Examiner* — David Isabella
*Assistant Examiner* — Ann Schillinger
(74) *Attorney, Agent, or Firm* — Medlen & Carroll, LLP (57) ABSTRACT A novel support system for bioprosthetic cardiac valves with heart shape commissural posts (18) and intercommissural conjunctions with long openings with oval closures (8), allows the better function of the valve by diminishing the forces applied on the leaflets during the cardiac cycle.

20 Claims, 7 Drawing Sheets

SUPPORT SYSTEM FOR BIOPROSTHETIC VALVES WITH COMMISURAL POSTS WITH HEART-SHAPED OPENINGS

FIELD OF INVENTION

The present invention relates to the field of surgical implants, and in particular to support systems or stents for bioprosthetic cardiac valves.

BACKGROUND

The human heart is a concave muscular organ, consisted of two atria and two ventricles, right and left. The atria communicate with the ventricles with the atrioventricular valves. The left atrium communicates with the left ventricle through the mitral valve and the right atrium communicates with the right ventricle through the tricuspid valve. At the output of the left ventricle, there is the aortic valve and at the output of the right ventricle there is the pulmonary valve. The function of the valve is to allow the one way flow through them. The valves consist of leaflets, three in number, apart the mitral valve where consists of two leaflets. The leaflets open to allow the blood to pass through them and close to prevent the regurgitation.

There are conditions that this mechanism fails with the result of non-physiological flow through them. In some congenital or acquired diseases, there is a hardening of the leaflets, more commonly due either to calcification or to rheumatic fever, which results to difficulty of fully opening of the leaflets and passing the blood through them. In these circumstances, the patient presents with the symptoms of valve stenosis.

In some circumstances, the leaflets do not come in conduct when they close, which results to blood leakage and the patient presents with the symptoms of valve regurgitation. In severe circumstances of stenosis or regurgitation, the diseased valve has to be replaced with a new prosthetic valve.

There are mainly two types of prosthetic valves for replacement: the mechanical and the biological. The mechanical valves has movable parts, mainly from graphite, while the biological valves are derived either from porcine aortic valve, or bovine pericardium (E. Andreas Agathos, Albert Starr: "Aortic Valve Replacement", Curr Prob Surg, July 1993: Vol XXX, No 357, pp 610-637), or from the aortic, pulmonary and the pericardium derived from seals (E. Andreas Agathos, "Human Cardiac Valve Placement with Marine Mammal Ventricular Outflow (Aortic or Pulmonary) Valves, U.S. Pat. No. 6,165,216, issued Dec. 26, 2000, and E. Andreas Agathos, "Human Cardiac Valve Replacement with Seal's Cardiac Valve (Aortic or Pulmonary), Greek patent No 1005718, issued on Jul. 11, 2007.

The bioprosthetic valves show an advantage over the mechanical valves, as they do not need the daily intake of anticoagulants, thus producing less incidence of thromboembolic episodes, hemorrhage and infectious endocarditis. The main disadvantage though is that they do not last as long as the mechanical valves do.

The bioprosthetic valves need a support system (stent) made of biomaterial, onto with the animal tissue is placed. There are many methods of placing animal tissue on a support system such as "Method of Leaflet Attachment for Prosthetic Heart Valves", U.S. Pat. No. 4,501,030, issued Feb. 26, 1985, "Tissue Heart Valves and Stent", U.S. Pat. Nos. 5,163,955, 5,423,887 and 5,489,298 to Love et al and "Prosthetic Heart Valve with Slit Stent", U.S. Pat. No. 6,936,067, issued on Aug. 30, 2005 to Buchanan; Eric S.

SUMMARY OF THE INVENTION

The present invention relates to the field of surgical implants, and in particular to support systems or stents for bioprosthetic cardiac valves. In one embodiment, the present invention contemplates a support system for bioprosthetic cardiac valves comprising an inflow opening defined by an inferior surface of the support system, an outflow opening defined by a superior surface of the support system, three commissural posts, each post having a single heart shaped (e.g. approximately triangular) opening, and intercommissural conjunctions with horizontal openings with oval closures positioned at a level above said inferior surface, wherein each single heart shaped opening is of a size such that it extends from below said superior surface toward said inferior surface to a level equal to or greater (i.e. lower) than said horizontal openings, and wherein each single horizontal opening has substantially parallel sides.

In another embodiment, the present invention contemplates a support system for bioprosthetic cardiac valves comprising an inflow opening defined by an inferior surface of the support system, an outflow opening defined by a superior surface of the support system, three commissural posts, each post having a single tear drop shaped (e.g. approximately triangular) opening, and intercommissural conjunctions with (two or four) horizontal openings with oval closures positioned at a level above said inferior surface, wherein each single tear drop shaped opening is of a size such that it extends from below said superior surface toward said inferior surface to a level less than or equal to (i.e. but not lower) than said horizontal openings, and wherein each single horizontal opening has substantially parallel sides.

It is preferred that there is less open area (created by the openings) in the intercommissural conjunctions than closed area (being the structure itself). Having large holes or openings in the conjunctions renders the whole support system (or stent) fragile and causes it to fail and break at the conjunctions.

REFERENCE NUMERALS 2 commissural posts
4 outflow orifice of the support system
6 heart shaped or tear drop shaped openings in the commissural posts
8 long horizontal openings with oval closures at the intercommissural conjunctions
10 outside surface of the support system
12 concave surface of the superior part of the commissural post
14 elevated edge of the commissural post
16 inflow orifice of the support system
18 support system for bioprosthetic cardiac valves
20 superior surface of the support system
22 inferior surface of the support system
24 intercommissural conjunction
25 small holes for stitching
26 single top hole for stitching

DEFINITIONS

Figure 5:
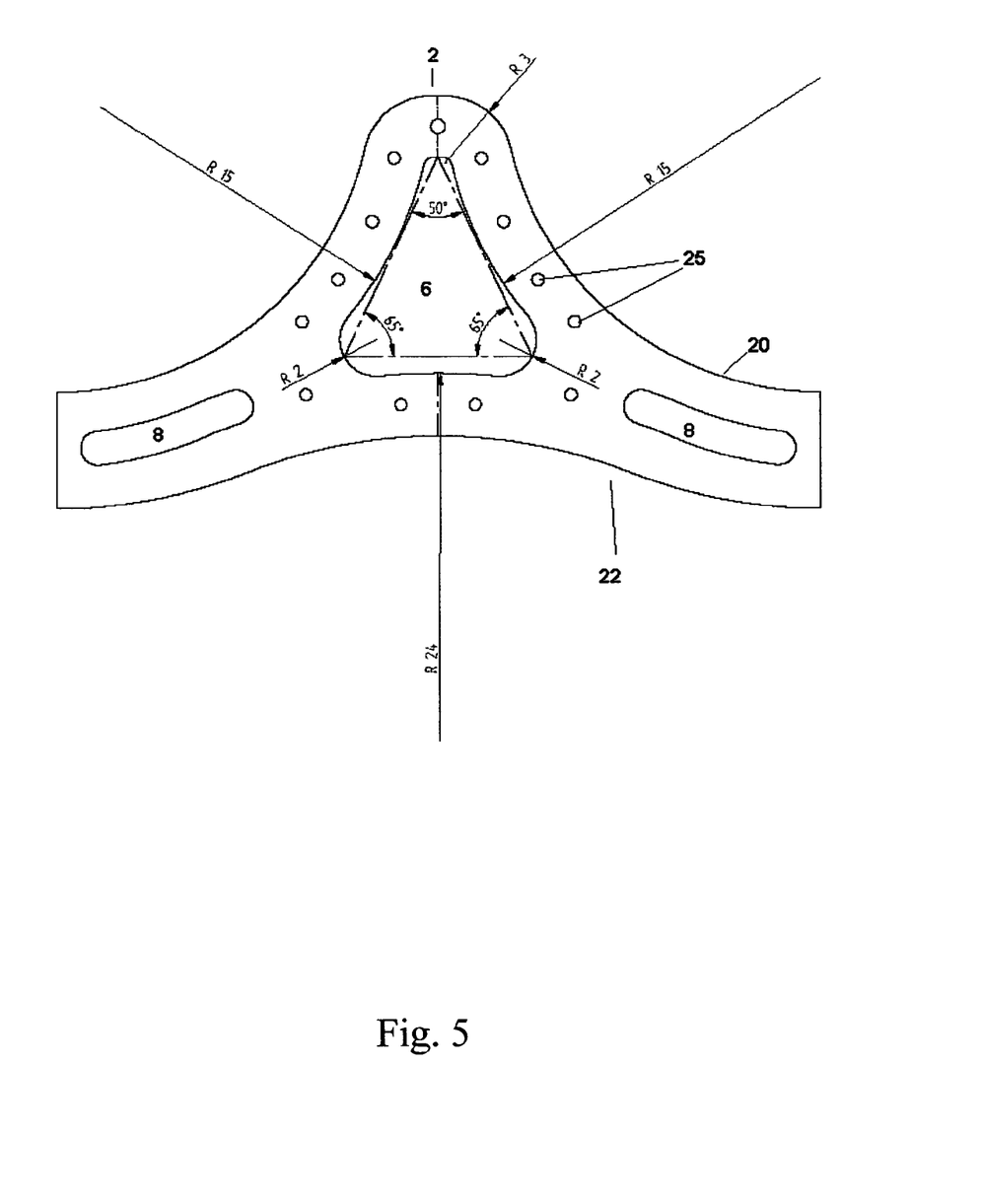
FIG. 5 A side view of one embodiment of the support system showing a single commissural post with a single tear drop shaped opening defined by an isosceles triangle (wherein the two equal angles, e.g. of 65 degrees, are at the bottom of the tear drop opening, and the top angle is e.g. 50 degrees).
Figure 6:
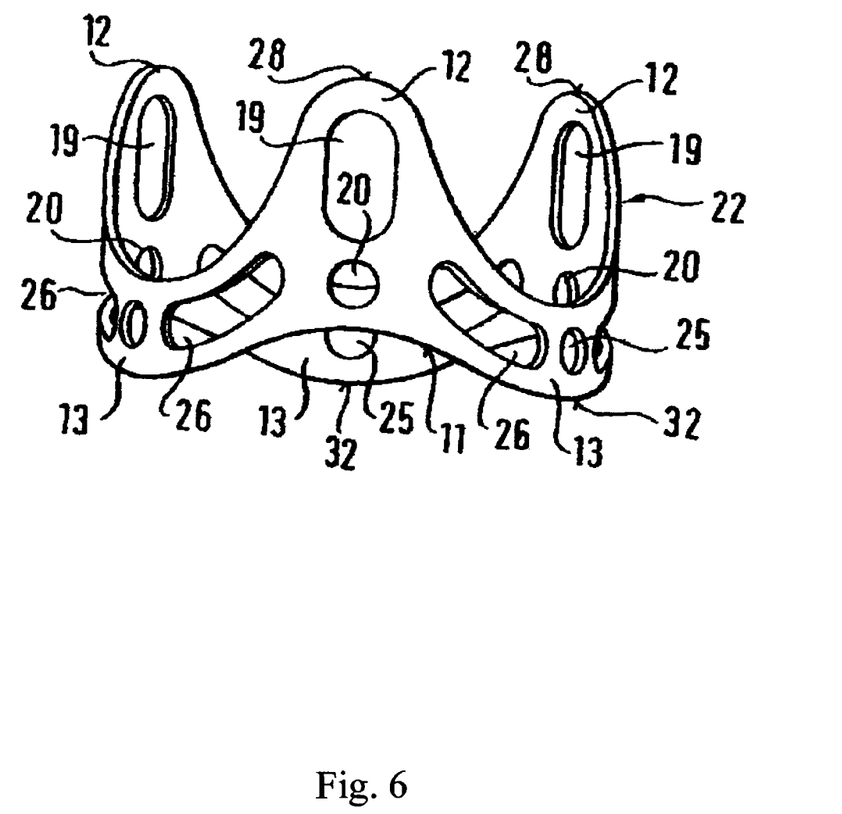
FIG. 6. A side view of a prior art support system (described in U.S. Pat. No. 4,626,255) showing three commissural posts, each with two large circular openings (in contrast to the single opening of the embodiments of the present invention described above), and three conjunctions with horizontal openings separated by single large circular opening.

As used herein, the term "heart shaped" or "tear drop shaped" can be viewed as approximately the shape of a triangle (see FIG. 5). In can be viewed as being formed by the intersection of five circles. For example, one can define the geometry that is produced when an arc of a circle with a radius of 3 mm, intersects at the top with two arcs of circles with a radius of 15 m each, while two other arcs of circles with radius of 2 mm each, intersect the aforementioned arcs of 15 mm radius, bilaterally and downwards. Thus an internal triangle is produced when the centers of each smaller arc are connected together. The top angle of the produced triangle can be 50 degrees and the other two 65 degrees each.

DESCRIPTION OF THE INVENTION AND EMBODIMENTS

Figure 1:
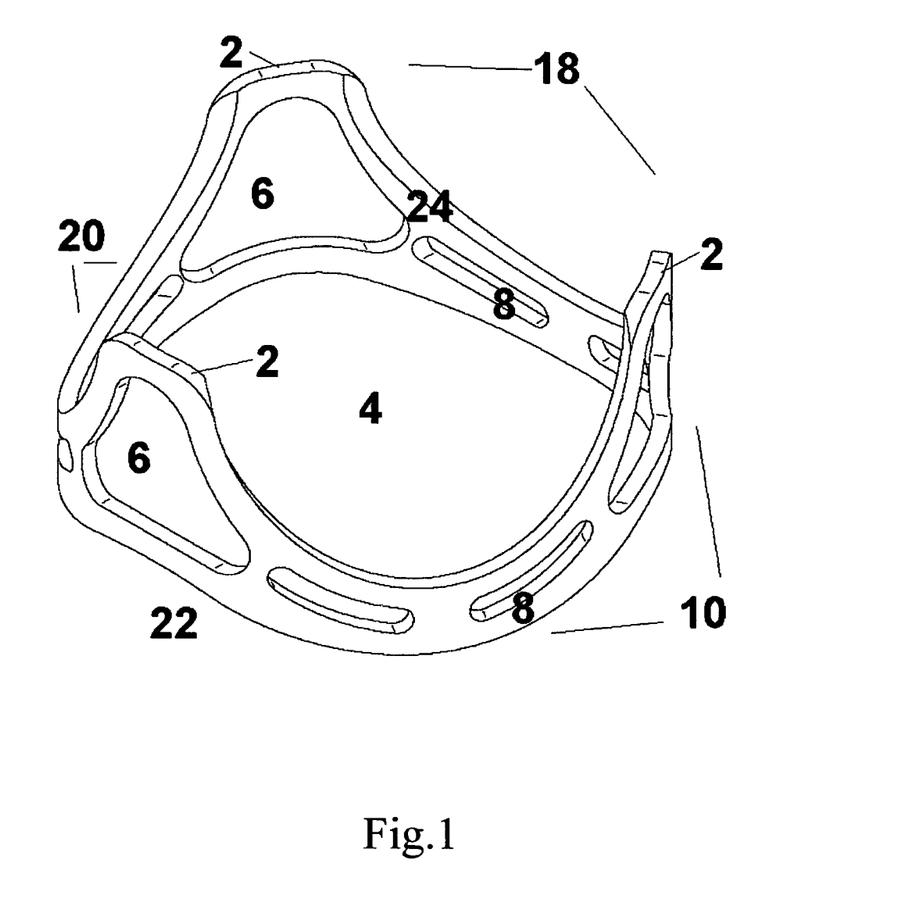
FIG. 1 A panoramic view of one embodiment of a new bioprosthetic support system of the present invention with single heart shaped (or approximately triangular) openings in three commissural posts and three intercommissural conjunctions, each intercommissural conjunction having two horizontal openings, each horizontal opening having parallel or substantially parallel side, such that the intercommissural conjunctions have less open area than closed area.
Figures 1, 7:
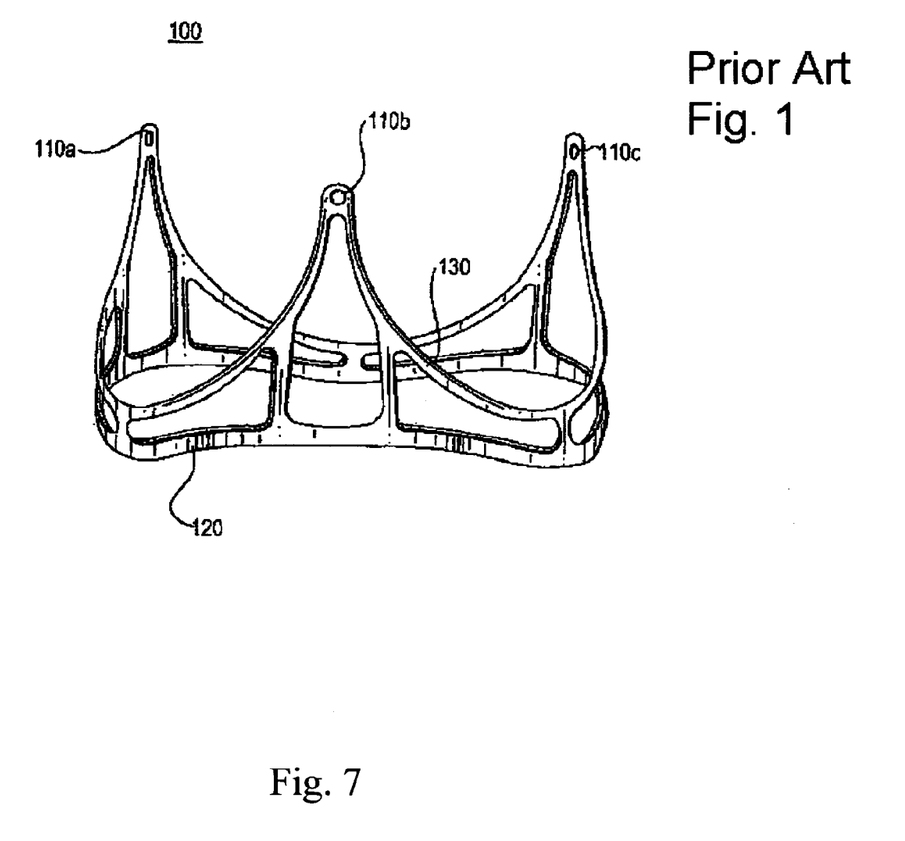
FIG. 7. A side view of a prior art support system (described in U.S. Publication No. 2008/0147179) showing three commissural posts, each with a single large bottle shaped opening, and intercommissural conjunctions with two large openings having non-parallel sides such that the intercommissural conjunctions have more open area than closed area. Such large openings in the conjunctions renders the support system fragile such that it will likely break at the conjunctions.

An illustrative embodiment of the present invention is shown in FIG. 1 which provides a panoramic view of the new support system of bioprosthetic cardiac valves 18 according to this novel invention. The outflow orifice 4 is shown, along with three commissural posts 2 with heart shaped openings 6 and the elevated edges 14 at the commissural posts 2. The elevated edges 14 of the commissural posts follow the normal geometry of the human cardiac valve, facilitating so the surgical implantation of the bioprosthetic valve. The commissural posts 2 have a heart shape appearance, allowing so the slight outwards movement of the placed biological tissue or from any origin made leaflets, so eliminating the catastrophic forces applied on the commissural posts and subsequently the leaflets. The commissural posts 2 are connected to each other with the intercommissural conjunctions 24. Between the outside surface of the support system 10 and the outflow orifice of the support system 4 and along the length of the intercommissural conjunctions 24 there are two long horizontal openings with oval closures 8, to facilitate the placement of support stitches through them. The size of these horizontal openings is such that there is less open area in the conjunctions 24 than closed area, in order to improve the strength of the support system.

Figure 2:
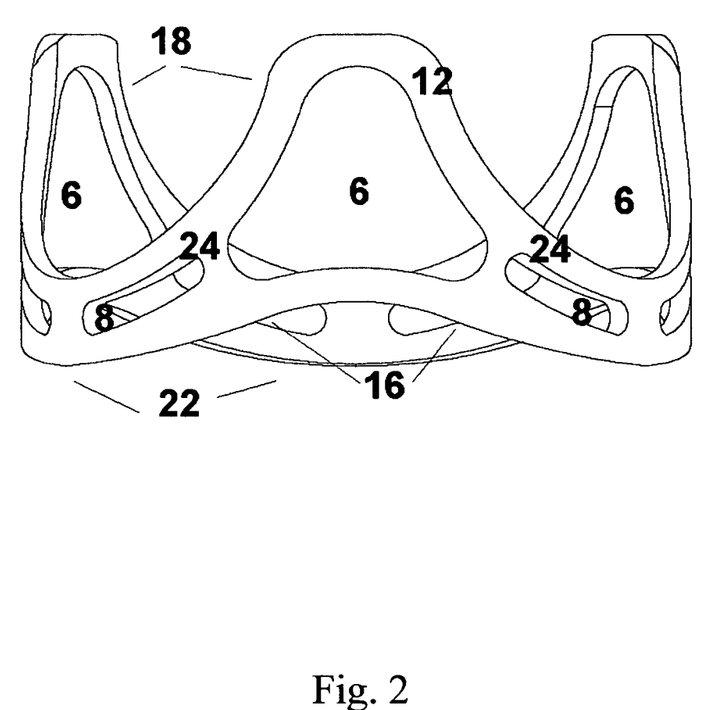
FIG. 2 A side view of one embodiment of a new support system of the present invention from outside inwards showing three heart shaped (or approximately triangular) openings each of a size such that it extends from below the superior surface toward the inferior surface to a level equal to or greater (i.e. lower) than said horizontal openings.

FIG. 2 is a view of one embodiment of the new bioprosthetic valve support system 18 from outside inwards. The concave surface of the superior part of the commissural post 12 allows the placement of biological tissue or from any origin made leaflets, in such a way as to diminish even more the catastrophic forces applied on them and the heart shaped openings 6 of the commissural posts 2 during the cardiac cycle. Along the intercommissural conjunctions 24 there are two long horizontal openings with oval closures 8, with such dimensions as to facilitate the placement of biological tissue or from any origin derived leaflets from the superior surface 20 and the inferior surface 22 of the support system.

Figure 3:
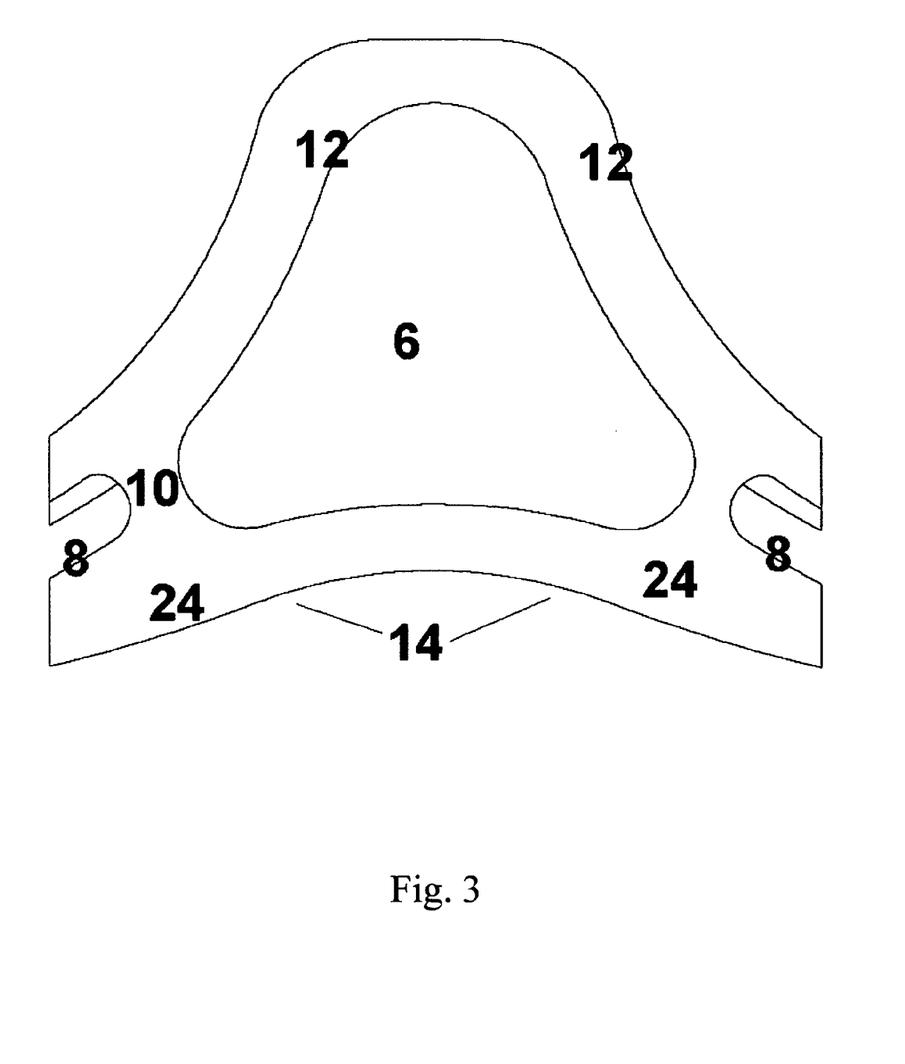
FIG. 3 An isolated view of one embodiment of a single heart shaped commissural post which is part of the support system of the present invention.

FIG. 3 shows a view of one embodiment of the heart shaped opening in the commissural post 6. The elevated edge 14 of the commissural post follow the geometry of a human valve. The heart shape commissural post 2, allows the slight outward movement of the placed biological tissue or from any origin made leaflets, so to diminish the friction forces applied on them during systole, facilitating so the opening of the valve. In the same matter the inward movement during diastole, facilitates the closure of the valve.

Figure 4:
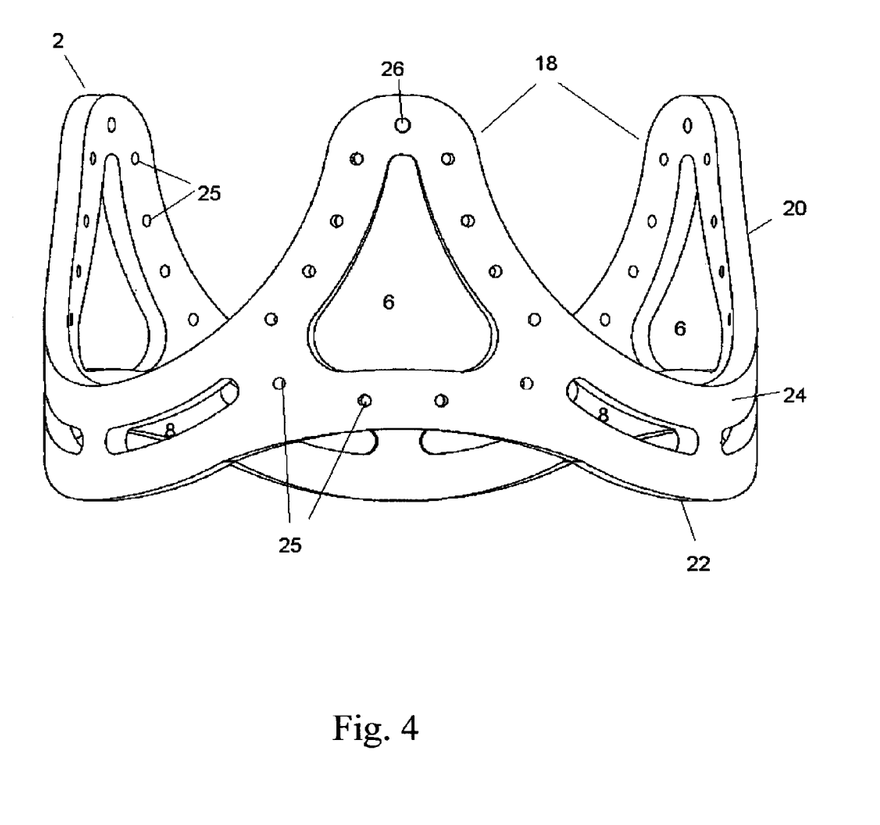
FIG. 4 A side view of another embodiment of the support system of the present invention showing three commissural posts with single tear drop (or approximately triangular) shaped openings surrounded by a plurality of small holes for stitching, wherein the size of the small holes for stitching are less than $1/20^{th}$ (and preferably less than $1/40^{th}$ and more preferably less than 1/60$^{th}$) the size of the single tear drop shaped opening, and wherein each tear drop shaped opening is of a size such that it extends from below the superior surface toward the inferior surface to a level less than or equal to (i.e. but not lower than) the level of said horizontal openings.

FIG. 4 is a side view of another embodiment of the support system 18 of the present invention showing three commissural posts 2, each with a single tear drop (or approximately triangular) shaped openings 6 surrounded by a plurality of small holes for stitching 25, wherein each tear drop shaped opening 6 is of a size such that it extends from below the superior surface 20 toward the inferior surface 22 to a level preferably less than (or equal to but not lower than) the level of said horizontal openings 8. Note that the size of these horizontal openings 8 is such that there is less open area in the conjunctions 24 than closed area, in order to improve the strength of the support system. The advantage of the smaller holes for stitching 25 is to facilitate the stitching of the tissue through them. Having more holes and of smaller size, it gives a better anchorage to the stitched tissue. Also it provides better stability of the stent as an entity. While not limited to particular sizes, the dimensions of these holes for stitching 25 are preferably 0.35 mm in diameter, with the exemption of a larger hole for stitching 26 at the top of each post 2 which is preferably 0.50 mm in diameter.

FIG. 5 is a side view of a portion of one embodiment of the larger support system (not shown) showing a single commissural post 2 with a single tear drop shaped opening 6 defined by an isosceles triangle (wherein the two equal angles, e.g. 65 degrees, are at the bottom of the tear drop opening), and wherein each tear drop shaped opening 6 is of a size such that it extends from below the superior surface 20 toward the inferior surface 22 to a level less than or equal to (i.e. but not lower than) the level of said horizontal openings 8.

The present invention consist a novel bioprosthetic cardiac valve support system with heart shape commissural posts. The function of this novel invention is to support the leaflets derived from tissue such as the aortic or pulmonary valve of the seal, the porcine aortic valve, leaflets made from pericardium of seal, bovine, equine, porcine or any other suitable tissue. At the same way the present invention may support leaflets made from any biocompatible material. The heart shape commissural post gives an extra opening at the valve, allowing the outwards or inwards movement of this part of the valve, reducing significantly the applied catastrophic forces, during systole or diastole of the cardiac cycle. The outward movement of the heart shape commissural post, during systole, facilitates the opening of the leaflets, while the inward movement of the commissural posts, during diastole, facilitates the better closure and avoidance of backflow of the blood.

It is not intended that the present invention be limited to particular dimensions. However, it is preferred that the "heart shaped" stent is produced in diameters from 15 mm up to 33 mm, as this is to resemble all the different sizes of human cardiac valves. The dimensions of this geometrical design, defined as "heart shape", can be modified from the given example, as for keeping the defined geometry to fit at the different sizes of the stent. The number of the horizontal openings at the conjunctions, while shown to be two in the drawings, can be four for the larger sizes of the stent. More specifically, for the stents sized 29 mm up to 33 mm, four horizontal openings are preferred so to facilitate the anchorage and stitching of the tissue and the dacron fabric.

The material of this new support system for bioprosthetic cardiac valves with heart shape commissural posts can be made from any biocompatible material, which is material compatible with blood and human tissue. Common medical materials can be used, such as those easily found in the market. These materials will be able to be sterilized with exposure to steam, gamma-radiation, chemical sterilization, such as glutaraldehyde, formaldehyde, ethylene oxide and propylene. The present invention can be made from hard or semi hard material, such as polymer, metal, ceramic, pyrolytic carbon and combination of the above. Proper polymers are the polyacetals, such as Delrin®, Celcon®, Tecaform™, different types of sulfons, polyetheramilids and polyetherketones. Other suitable synthetic polymers are the polyamids (nylon), polyester, polysteren, polyacryl, and vinyl polymers, such as polyethylene, polytetrafluorethylene (PTFE), and other analog synthetic materials.

Suitable metals for this new support system are biocompatible metals, such as stainless steel, titanium, cobalt alloys, such as Elgiloy®, Nitinol, which is a nickel-titanium alloy. Also materials such as ceramics can be used, such as pyrolytic carbon, carbides/silicon nitrides, metal carbides/nitrides, graphite, zircons and aluminum. Also, absorbable polymers, such as dextrane, zelatine, polyglycols, D,L-polylactic acid, D-lactic acid and glycolic acid.

The leaflets can be made either from tissue or from flexible polymers. Biomaterials that can be used for the present invention are solid tissues as well as decellalurized or modified tissues. Suitable tissues are the xenografts (such as the aortic and pulmonary valve of seal, porcine aortic valve, seal's pericardium, bovine, equine and porcine pericardium), homografts (from human to human) or autografts (from the same patient). The tissues can be treated with chemical compounds such as glutaraldehyde, formaldehyde, epoxids, diimines, aldehydes, anticalcification agents. Suitable polymers for making the leaflets are for example the synthetic polymers, as well as biological polymers or combination of both. Synthetic polymers are for example the polyamids, polyesters, polyacryls, vinyl polymers and the polyacetals (i.e. Delrin®).

The new support system for bioprosthetic valves with heart shape commissural posts of the present invention can be covered externally with polytetrafluoroethylene (PTFE) or cloth, tissue, or any other material so to minimize the deterioration of the leaflets and the formation of thrombus. For this reason one of the preferred embodiments of the present invention, is that the support system at the commissural posts may has small openings, to facilitate the positioning and stitching of the PTFE, cloth, tissue or any other suitable material. Also this new support system may have a sewing ring at the external surface to facilitate the surgical implantation of the bioprosthetic valve in humans. The material of the sewing ring that allows the passage of surgical stitches through it can be of silicon, cloth, polyester and other suitable materials.

The present support system of bioprosthetic valves with heart shape commissural posts offers an advantage over the commonly used support systems, and this is the large heart shaped openings at the commissural posts. These large openings allows the slight movement of the material or the leaflets made from biocompatible materials, inwards and outwards, during the cardiac cycle. The outwards movement during systole facilitates the opening of the leaflets, while the inwards movement during diastole, allows the better closure of the leaflets, avoiding the regurgitation of the blood. The large heart shape openings at the commissural posts, allows the evenly distribution of forces applied on the leaflets during the cardiac cycle, which forces are responsible for the deterioration of the bioprosthetic valves.

This novel support system of the present invention, facilitates the surgical implantation of the bioprosthetic valves, due to the fact that the support system maintain the normal geometry of the human valve, because of the rather hard material, and facilitates the surgical implantation with a continuous stitch or interrupted stitches, surgical techniques widely used ("Tissue Heart Valves", ed. By M. I. Ionescu, publisher Butterorth Inc., Boston, Mass., U.S.A., 1979, pp. 32-34, 107-109, 177).

The invention claimed is:

1. A support system for bioprosthetic cardiac valves constructed of a material comprising an inflow opening defined by an inferior surface of the support system, an outflow opening defined by a superior surface of the support system, three commissural posts, each post having a single heart shaped opening, and intercommissural conjunctions with two horizontal openings with oval closures positioned at a level above said inferior surface, wherein each single heart shaped opening is of a size such that it extends from below said superior surface toward said inferior surface to a level equal to or greater than said horizontal openings, and wherein each single horizontal opening has substantially parallel sides, such that the intercommissural conjunctions have less open area than closed area.

2. The support system of claim 1, where the material of construction is polyacetal.

3. The support system of claim 1, where the material of construction is polymer.

4. The support system of claim 1, where the material of construction is metal or metal alloy.

5. The support system of claim 1, where said system is covered totally with polytetrafluoroethylene (PTFE).

6. The support system of claim 1, where said system is covered totally with cloth.

7. The support system of claim 1, where said system is covered totally with tissue.

8. The support system of claim 1, where a sewing ring is placed perimetrical.

9. The support system of claim 8, where the sewing ring consists of polymer.

10. The support system of claim 8, where the sewing ring consists of cloth.

11. The support system of claim 8, where the sewing ring consists of silicon.

12. The support system of claim 1, each single heart shaped opening is of a size such that it extends from below said superior surface toward said inferior surface to a level greater than said horizontal openings.

13. A prosthetic valve, comprising the support system of claim 1 and flexible leaflets.

14. A prosthetic valve of claim 13, where the flexible leaflets consist of tissue.

15. A prosthetic valve of claim 13, where the flexible leaflets consist of suitable treated tissue.

16. A prosthetic valve of claim 13, where the flexible leaflets consist of polymers.

17. A support system for bioprosthetic cardiac valves comprising an inflow opening defined by an inferior surface of the support system, an outflow opening defined by a superior surface of the support system, three commissural posts, each post having a single tear drop shaped opening, and intercommissural conjunctions with horizontal openings with oval closures positioned at a level above said inferior surface, wherein each single tear drop shaped opening is of a size such that it extends from below said superior surface toward said inferior surface to a level equal to said horizontal openings, and wherein each single horizontal opening has substantially parallel sides, wherein there is less open area in the intercommissural conjunctions than closed area.

18. The support system of claim 17, wherein each conjunction comprises two horizontal openings.

19. The support system of claim 17, further comprising a plurality of small holes for stitching surrounding the tear drop shaped opening of each post.

20. The support system of claim 17, wherein the bottom of each single tear drop shaped opening has two equal angles of 65 degrees.

\* \* \* \* \*